United States Patent [19]
Gish et al.

[11] 3,975,367
[45] Aug. 17, 1976

[54] ARABINOFURANOSYL N⁴-AMINOACYL CYTOSINE CONTAINING COMPOUNDS

[75] Inventors: Duane T. Gish, Portage; Gary D. Gray, Pavilion Township, Kalamazoo County; William J. Wechter, Kalamazoo, all of Mich.

[73] Assignee: The Upjohn Company, Kalamazoo, Mich.

[22] Filed: Aug. 30, 1974

[21] Appl. No.: 501,886

Related U.S. Application Data

[62] Division of Ser. No. 150,918, June 8, 1971, abandoned.

[52] U.S. Cl. .................... 260/112.5 R; 424/177; 424/180; 536/23
[51] Int. Cl.² ............. C07C 103/52; C07H 19/06; C07H 19/08
[58] Field of Search ............ 260/211.5 R, 112.5

[56] References Cited
UNITED STATES PATENTS

| | | |
|---|---|---|
| 3,089,869 | 5/1963 | Mauvernay ................ 260/211.5 R |
| 3,155,647 | 11/1964 | Dutcher et al. .............. 260/211.5 R |
| 3,309,359 | 3/1967 | Duschinsky et al. ......... 260/211.5 R |
| 3,755,295 | 8/1973 | Verheyden et al. .......... 260/211.5 R |

*Primary Examiner*—Johnnie R. Brown
*Attorney, Agent, or Firm*—John J. Killinger; Roman Saliwanchik

[57] ABSTRACT

Certain new 1-(3′,5′-O-Variable-β-D-arabinofuranosyl)-N⁴-α-aminoacylcytosines, for example, 1-(5′-O-palmitoyl-β-D-arabinofuranosyl)-N⁴-[N$^\alpha$-[N-(tert-butoxycarbonyl)glycyl]-L-arginyl]cytosine hydrochloride, have been found active against neoplastic cells, viruses, and as immunosuppressants. The 3′-O-, or 5′-O-, variability includes the hydrogen atom and acyl groups. The N⁴-α-aminoacyl group comprises α-amino acids, N-protected α-amino acids, and similar peptidyl sequences of α-amino acids. Acid addition salts are an embodiment of the invention.

12 Claims, No Drawings

ARABINOFURANOSYL N⁴-AMINOACYL CYTOSINE CONTAINING COMPOUNDS

This is a division of application Ser. No. 150,918, filed June 8, 1971, now abandoned.

SUMMARY OF THE INVENTION

This invention pertains to new chemical compounds and to a process for preparing the same. The invention is more particularly directed to new 1-(3',5'-O-Variable-$\beta$-D-arabinofuranosyl)-N⁴-$\alpha$-aminoacylcytosines, and a process for preparing the same. The new compounds have the following general structural formula:

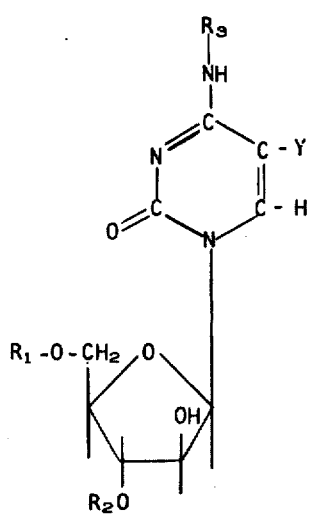

wherein $R_1$ and $R_2$ are hydrogen, or an acyl group comprising up to 21 carbon atoms; Y is hydrogen, halogen, alkyl of from 1 to 4 carbon atoms, inclusive, hydroxyalkyl of from 1 to 4 carbon atoms, inclusive, or haloalkyl of from 1 to 4 carbon atoms, inclusive; and $R_3$ is an $\alpha$-aminoacyl group comprising a single $\alpha$-amino acid or up to 10 of the common $\alpha$-amino acids linked as peptides.

The new 1-(3',5'-O-Variable-$\beta$-D-arabinofuranosyl)-N⁴-$\alpha$-aminoacylcytosines of this invention are biologically active nucleosides like 1-$\beta$-D-arabinofuranosylcytosine (cytarabine or CA) itself. The new compounds are active against neo-plastic cells and can be used as anti-tumor agents. The compounds are also immunosuppressants and can be used to prevent host rejection of foreign tissue transplants. The compounds are also active against viruses and can be used to suppress propagation of viruses, for example, Herpes simplex virus, adenoviruses, and cytomegalo viruses.

Acid addition salts of the free base compounds described in Formula I have the same biological activities when properly administered. No criticality attaches to proper administration other than the ordinary skill of medical practice to ascertain the efficacy of any unusual acid addition salt and decide upon the dosage to be administered. Applicants here purposefully avoid the designations "pharmacologically acceptable" or "pharmaceutically acceptable" acid addition salts that are frequently seen. These designations inicate no more than the well-known fact that some acid addition salts are frequently used in medicine, while others are not commonly used or might cause undesirable side reactions unless carefully dosed. The dominant consideration being that substantially all acid addition salts properly administered to an animal's body will be changed to the free base, and the salt forming anion will be detoxicated via metabolic pathways. The "frequently used" acid addition salts are preferred.

The conceptual basis for the scope of $R_1$, $R_2$, $R_3$, and Y is prior experience with 3' and 5' "substituted" CA and from observations in preliminary testing of some new 1-(3',5'-O-Variable-$\beta$-D-arabinofuranosyl)-N⁴-$\alpha$-aminoacyl-cytosines of this invention. In accordance with applicants' experience and observations the following representations are made:

The acyl groups comprising up to 21 carbon atoms that are representative include those of organic carboxylic acids,

wherein R can be a straight- or branched-chain aliphatic group of from 1 through 20 carbon atoms, inclusive; a monocyclic or bicyclic aromatic group of from 6 to 10 carbon atoms, inclusive; an araliphatic group of from 7 to 12 carbon atoms, inclusive; a cycloaliphatic group of from 3 to 12 carbon atoms, inclusive, and adamantoyl.

The foregoing designation "monocyclic or bicyclic aromatic group of from 6 to 10 carbon atoms, inclusive," includes phenyl, p-tolyl, 3,5-xylyl, 2,4,6-trimethylphenyl, p-tert-butylphenyl, p-anisoyl, m-phenyl, o-chlorophenyl, 3,4-dibromophenyl, p-trifluoromethylphenyl, 1-naphthyl, and 2-naphthyl.

The designation "cycloaliphatic group of from 3 to 12 carbon atoms, inclusive," includes cyclopropyl, cyclobutyl, cyclopentyl, cyclohexyl, cycloheptyl, cyclooctyl, (3-methylbutyl)cyclohexyl, and 3,5-diisopropylcyclohexyl.

The designation "araliphatic group of from 7 to 12 carbon atoms, inclusive," includes inter alia benzyl, phenethyl, 3-phenylpropyl, and 2-phenylhexyl.

The "$\alpha$-aminoacyl group comprising a single $\alpha$-amino acid or up to 10 of the common $\alpha$-amino acids linked as peptides" that is representative of the variable $R_3$ includes, e.g., glycyl, valyl, alanyl, $\alpha$-aminobutyryl, leucyl, norleucyl, ornithyl, lysyl, arginyl, seryl, threonyl, cysteyl, cystyl, methionyl, phenylalanyl, tyrosinyl, histidyl, tryptophanyl, prolyl, hydroxyprolyl, N$^\alpha$ -[N-(tert-butoxycarbonyl)glycyl]arginyl, N$^\alpha$ -(glycyl)arginyl, N$^\alpha$ -(tert-butoxycarbonyl)arginyl, N$^\alpha$ -[N-[N-(tert-butoxycarbonyl)-glycyl]glycyl]arginyl, N$^\alpha$ -[N-[N-[N-(tert-butoxycarbonyl)-glycyl]glycyl]glycyl]arginyl, N$^\alpha$ -[N-[N-[N-[N-(tert-butoxy-carbonyl)glycyl]-glycyl]glycyl]glycyl]arginyl, N$^\alpha$ -[N-(tert-butoxycarbonyl)glycyl]lysyl, N$^\alpha$ -[N-[N-(tert-butoxycarbonyl)-glycyl]glycyl]lysyl, N$^\alpha$ -[N-[N-(glycyl)glycyl]glycyl]arginyl, N$^\alpha$ -[N-[N-[N-(glycyl)glycyl]glycyl]glycyl]arginyl, N$^\alpha$ -(glycyl)lysyl, arginyl, lysyl, N$^\alpha$ -[N-(tert-butoxycarbonyl)-seryl]arginyl, N$^\alpha$ -(seryl)arginyl, N$^\alpha$ -[N-[N-[N-[N-[N-(tert-butoxycarbonyl)-glycyl]glycyl]glycyl]glycyl]glycyl]-glycyl]arginyl, $N^\alpha$-[N-[N-(glycyl)glycyl]seryl]arginyl, $N^\alpha$-[N-(glycyl)seryl]arginyl, $N^\alpha$-[N-[N-(tert-butoxycarbonyl)-glycyl]seryl]arginyl, N-[N-[N-(tert-butoxycarbonyl)glycyl]-glycyl]phenylalanyl, N-(tert-butoxycarbonyl)phenylalanyl, N-[N-[N-(tert-butoxycarbonyl)-glycyl]seryl]phenylalanyl, N-[N-(tert-butoxycarbonyl)glycyl]phenylalanyl, N-[N-(glycyl)-glycyl]-phenylalanyl, and N-[N-[N-(tert-butoxycarbonyl)-seryl]glycyl]glycyl]phenylalanyl.

The new 1-(3′,5′-O-Variable-α-D-arabinofuranosyl)-$N^4$-(α-aminoacyl)cytosines of this invention (compounds according to Formula I) are prepared by reacting a 1-(3′-O- or 5′-O-blocked-β-D-arabinofuranosyl)-cytosine with an α-amino acid or a di-, tri-, or polypeptide thereof in the presence of a peptide bond-forming reagent. Any organic solvent medium inert as to the reactants and product can be used. Suggested ones are dimethylformamide, dimethylacetaminde, and hexamethylphosphoric triamide. Various concentrations of the 1-(3′-O- or 5′-O-blocked-β-D-arabinofuranosyl)cytosine can be employed, and a suggested concentration range is 1% to 40%, preferably 5% to 20%.

The organic solution of the 1-(3′-O- or 5′-O-blocked-β-D-arabinofuranosyl)cytosine is preferably cooled to about 5° C. for the reaction, but the temperature of the reaction medium is not critical, and any temperature in the range of −20° C. up to 50° C. is considered practical. Higher or lower temperatures could of course be used.

To the preferably cooled organic solution is added an equivalent amount of the amino acid or peptide reactant, along with about 1 to about 5 equivalents of the peptide bond forming reagent. The reaction proceeds under these conditions, but stirring the reaction mixture is recommended.

In a preferred embodiment of the foregoing reaction process, the guanido functional group of arginine or an arginyl peptide is protected by using an acid addition salt form of the CA or arginine. The hydrochloride salt is suitable and preferred. Likewise, a free amino group of a peptide or an amino acid should be protected by an amino-protecting group such as tert-butoxycarbonyl. Such an amino-protecting group can be removed later, if desired, by acid hydrolysis. Trifluoroacetic acid is suitable and effects the removal in a short time at about 25° C. Hydrochloric acid at about 1 N concentration is also effective.

The compounds of this invention having free amino groups form acie addition salts with acids. Preferably, acid addition salts are prepared with mineral acids and organic acids having a pKa about 2 or lower. Representative mineral acids include hydrochloric, sulfuric, phosphoric, and hydrobromic. Representative organic acids include acetic, propionic, formic, glutaric, glutamic, oxalic, tartaric, salicylic, and trihydroxybenzoic.

Acid addition salts are prepared by dissolving or otherwise dispersing the selected 1-(3′,5′-O-Variable-β-D-arabinofuranosyl)-$N^4$-(α-aminoacyl)cytosine in a liquid medium, e.g., methanol and adding an eqivalent amount of a selected acid. The acid addition salt is recovered by evaporation in vacuo of the solvent. The product so obtained may be purified, if desirable, by recrystallization or by chromatography over a suitable support such as silica gel. It will be noted in the examples given below that in many cases the method of preparation allows the isolation of the synthetic product directly in the form of an acid addition salt product.

Referring back to the primary reaction mixture comprising a 1-(3′-O- or 5′-O-blocked-β-D-arabinofuranosyl)cytosine, an amino acid or a peptide reactant, and the peptide bondforming reagent, the course of the reaction can be followed by thin layer chromatography. When the reaction is complete or substantially complete, the reaction mixture can be filtered in order to remove any insoluble materials. The desired product is recovered by removing the medium by evaporation or by distillation under reduced pressure. The product compound is purified by any of the many appropriate methods for purifying nucleosides, e.g., solvent crystallization, chromatographic separation, differential solubilities in immiscible solvents and other procedures familiar to those skilled in the art.

The starting 1-(3′-O- or 5′-O-blocked-β-D-arabinofuranosyl)cytosines for the process of this invention are prepared in accordance with a variety of methods. In general 5′-O-blocked CA starting compounds are prepared by initislly blocking or protecting the 4-amino group of the cytosine base with a β,β,β-trihaloethoxycarbonyl halide, and finally reacting the 4-amino-blocked or protected CA with a reagent that substitutes on the 5′-position. The 4-amino-blocking group is then removed.

The β,β,β-trihaloethoxycarbonyl halide is a preferred 4-amino-blocking or protecting group although other such can be used. The term "halo" thereof includes bromo and chloro. The term "halide" thereof includes chloride, bromide, and iodide.

The initial blocking or protection of the 4-amino-position is not essential but it promotes efficiency and economy. The amount of the substituting reagent, e.g., esterifying reagent needed is minimized as well as reducing wastage of the CA component.

An esterificatin blocking of the 5′-O-position is shown in the following reaction sequence wherein X is chloro or bromo;

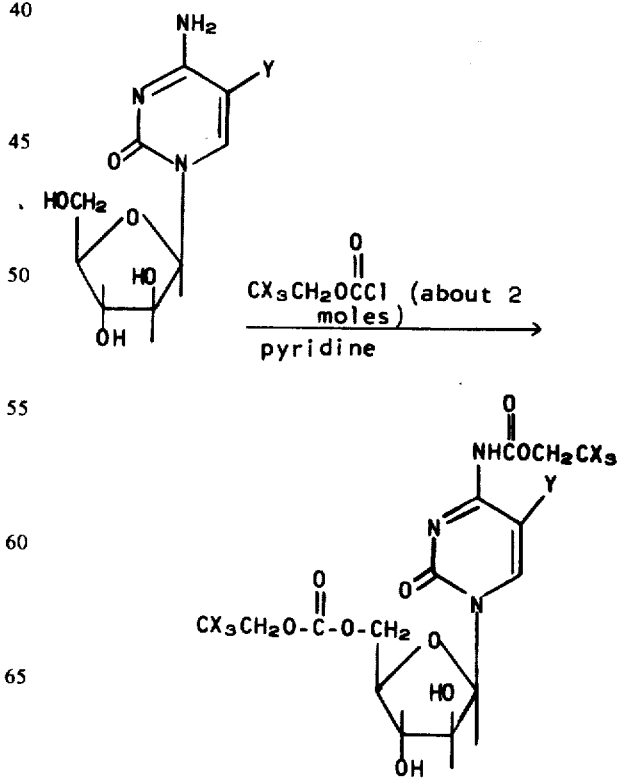

base hydrolysis →
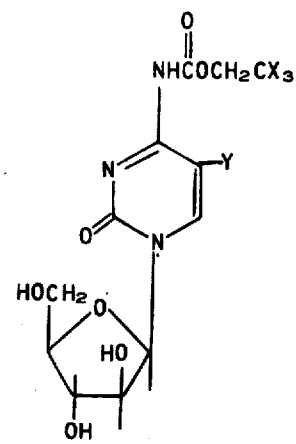
acylating agent
e.g., acid anhydride →
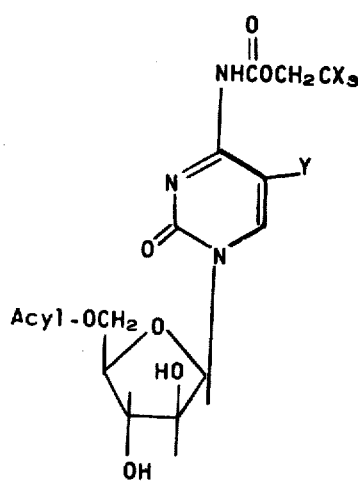
zinc, acetic acid →
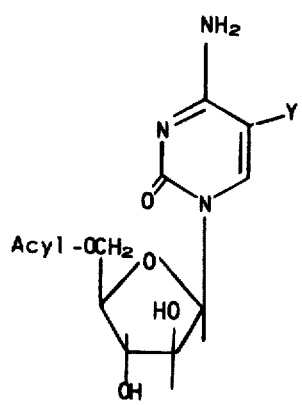

In the foregoing reaction steps variations can be employed. For example, in step one, a 5'-O-trityl CA could be used instead of the depicted CA itself. In accordance with this variation, the 5'-O-trityl group is removed by known methods, e.g., acid hydrolysis with 80% aqueous acetic acid to obtain the 4-amino protected CA.

As shown, the 4-amino protected CA can be reacted with an acylating agent to form any desired 5'-O-acylated CA starting compound after removing the β, β, β-trihaloethoxy-carbonyl protecting group. A recommended procedure for removing the group is to treat a 5'-O-acylated-4-amino(trihaloethoxylated) CA with metallic zinc in methanol. Variations include use of zinc dust and acetic acid, e.g., 80–90% acetic acid; and zinc chloride or zinc acetate in methanol. Acylation at the 5'-O-position is accomplished by conventional methods using, e.g., acid anhydrides, acyl halides, hydrocarbyl isocyanates and hydrocarbyl chloroformates.

Acylation at the 5'-O-position of CA can also be accomplished by reacting CA with a suitably activated acid, e.g., an acid chloride in the presence of a protonating agent. Thus illustratively, CA.HCl can be reacted with an acyl halide, e.g., palmitoyl chloride. In a representative reaction, an equivalent of palmitoyl chloride is mixed with CA.HCl as a solution in dimethylacetamide or dimethylformamide. After the reaction is substantially complete (several hrs. at 25° C.) the solvent is removed by evaporation under reduced pressure. The residual oil thus obtained is triturated with aqueous sodium bicarbonate, and the solid that forms is collected on a filter. After washing the filter cake with water and drying, it is washed with ethyl acetate. Recrystallization or other purification procedures can be used to obtain the product in pure form.

When one desires to prepare a 1-(3'-O- or 3',5'-O-blocked-β-D-arabinofuranosyl)-$N^4$-(α-aminoacyl)-cytosine according to Formula I, procedures similar to those already described are used. In the preparation of 3',5'-O,O-diesters according to Formula I a protonated CA is reacted with an acylating agent, e.g., anhydrides or acid halides of carboxylic acids, in the presence of a solvent. Suitable protonated CA's include acid addition salts such as the hydrochloride, hydroiodide, sulfate, phosphate, benzenesulfonate, and the like. Suitable solvents include dimethylacid amide, diethylformamide, dimethylformamide, and propionamide. A convenient temperature for this reaction is 25° C. Two molar equivalents or slightly more of the acylating agent should be used for each mole of the protonated CA. About 2.5 molar equivalents is preferred. The 2',3',5'-O,O,O-triacylated compound will be produced if too much acylating agent is used. The desired 3',5'-O,O-diesters are then obtained by neutralizing the acid addition salt to give the free bases, and separating the free bases by chromatography.

Neutralization is readily effected with a mildly alkaline reagent, e.g., an alkali metal bicarbonate. Representative ones are sodium and potassium bicarbonate. The organic bases pyridine and lutidine can also be used.

1-(3'-O- or 3',5'-O,O-blocked-β-D-arabinofuranosyl)-$N^4$-(α-aminoacyl)cytosines are also prepared by acylating a protonated 2,2'-cyclo CA. The starting 2,2'-cyclo CA is prepared according to the procedure described by D. T. Gish, G. L. Neil and W. J. Wechter, J. Med. Chem., in press (1971). Preferentially the 2,2'-cyclo CA is protonated and then acylated in the described way with either slightly more than one or slightly more than two molar equivalents of acylating agent. This reaction must be effected in the absence of water, alcohol, and especially bases because the cyclonucleoside is readily cleaved.

If desired, the protonated form of the CA can be obviated and direct triacylation of the 3'-, 5'- and 4-aminopositions effected. The 4-aminoacyl linkage is then hydrolyzed to give the desired 1-(3',5'-O,O-acylated-β-D-arabinofuranosyl)cytosine.

In accordance with another variation, a 2,2'-cyclo CA acid addition salt is 5'-O-tritylated and this 5'-O-tritylated-2,2'-cyclo CA acid addition salt is acylated with about one to about one and one-half molar equivalents of the acylating agent. The acylation reaction proceeds most readily at temperatures in the range of 40° to 50° C. Subsequently, the 5'-O-trityl group is removed by acidic hydrolysis, e.g., 80% glacial acetic acid and 20% water. Trifluoroacetic acid at a concentration of about 1% to about 3% in chloroform can also be used. The 2,2'-cyclolinkage is readily cleaved by water or mild base.

The foregoing general and special methods of obtaining starting materials are not exhaustive and further variations will be apparent to those skilled in the art. Representative operable preparations are described in the following examples, and these will provide reference guidelines for those of ordinary skill in the art.

EXAMPLE 1

Preparation of
1-(5'-O-palmitoyl-β-D-arabinofuranosyl)-$N^4$-
[$N^\alpha$ -[N-(tert-butoxycarbonyl)-glycyl
]-L-arginyl]cytosine hydrochloride A solution consisting of 15.5 g. (0.03 mole) 1-(5'-O-palmitoyl-β-D-arabinofuranosyl)cytosine hydrochloride, 100 ml. dimethylformamide and, last added, 9.9 g. (0.03 mole) $N^\alpha$ -[N-(tert-butoxycarbonyl)glycyl]-L-arginine was cooled to about 0° C. in an ice bath before 7.4 g. dicyclohexylcarbodiimide was added. Maintaining the ice-bath temperature, the reaction mixture was stirred continuously for 90 hrs. The reaction mixture was then filtered and the residue on the filter (dicyclohexylurea) was washed with dimethylformamide. After combining the dimethylformamide wash with the original filtrate, an equal volume of water and one l. of ethyl acetate were added. A crystalline solid that formed was collected on a filter, washed with a mixture consisting of 1 part dimethylformamide, 4 parts ethyl acetate, and 1 part water, and finally washed with diethyl ether. The filtrate was saved. The washed solid was identified as 1-(5'-O-palmitoyl-β-D-arabinofuranosyl)cytosine starting compound by thin layer chromatography on silica gel using a solvent mixture consisting of 65 parts methyl ethyl ketone, 20 parts acetone, and 15 parts water. The organic ethyl acetate phase of the saved filtrate was separated from the water phase and washed with 200 ml. water to effect crystallization of additional 1-(5'-O-palmitoyl-β-D-arabinofuranosyl)cytosine. The separated water phase and the wash water were combined and concentrated under reduced pressure to an oil, which by TLC analysis contained the desired product as well as some of the starting compounds. Accordingly, about 18.0 g. of the oil was dissolved in 50 ml. of a solvent system consisting of 72 parts methyl ethyl ketone, 20 parts acetone, and 8 parts water. The solution was poured onto a column of silica gel (45 mm. × 115 cm., amounting to 800 g.). The chromatogram was developed with 500 ml. of the solvent, and then 25 ml. fractions were collected. Fractions 71 through 160 contained the desired product. They were combined and the solution was concentrated by evaporating the solvents under reduced pressure. The concentrate was lyophilized to give 9.0 g. of 1-(5'-O-palmitoyl-β-D-arabinofuranosyl)-N⁴-[Nα -[N-(tertbutoxycarbonyl)-glycyl]-L-arginyl]cytosine hydrochloride characterized by an optical rotation $[\alpha]_D^{25} = +62°$ (c = 1 in $H_2O$).

Analysis: Calc'd. for $C_{28}H_{66}N_8O_{10} \cdot HCl$: C, 54.89; H, 8.12; N, 13 48; Cl, 4.26. Found: C, 54.93; H, 8.32; N, 13.47; Cl, 4.69.

I. R. Spectrum:
NH/OH/NH, 3340–3160; C=O/C=C/C=N/NH, def. "amide II" ~1720, ~1650, ~1560; C-O/C-N/other, 1310, 1250, 1165, 1105, 1070, 1050, 940, 865, 805.

EXAMPLE 2

Preparation of
1-(5'-O-palmitoyl-β-D-arabinofuranosyl)-N⁴-[N-[N-[N-(tert-butoxycarbonyl)glycyl]glycyl]-L-phenylalanyl]cytosine A solution consisting of 4.82 g. (0.01 mole) 1-(5'-O-palmitoyl-β-D-arabinofuranosyl)cytosine and a solvent mixture consisting of equal parts dimethylformamide and dioxane was obtained by warming slightly. This solution was cooled to 5° C. and 3.8 g. (0.01 mole) N-[N-[N-(tertbutoxycarbonyl)glycyl]glycyl]-L-phenylalanine was added, followed by 2.47 g. (0.012 mole) dicyclohexylcarbodiimide. This reaction mixture was stirred continuously for 4 days while the temperature was maintained at 5° C. The reaction mixture was then filtered in order to remove the dicyclohexylurea that had formed. The solvents were removed from the filtrate by evaporation under reduced pressure. The residual oil thus obtained was dissolved in 25 ml. diethyl ether, and the ether solution was set aside in a refrigerator for about 16 hrs. Some solids that separated were removed by filtering, and the filtrate was concentrated to a glass by removing the ether by evaporation. The glassy residue was dissolved in 50 ml. of a solvent system consisting of 72 parts methyl ethyl ketone, 20 parts acetone, and 8 parts water, and the solution was poured onto a column of silica gel 45 mm. × 115 cm. amounting to 800 g. which had been equilibrated with this same solvent. The chromatogram was developed with about 100 ml. of the solvent mixture, and then 10 ml. fractions were collected. After combining fractions 75 through 105, and concentrating the solution by evaporation of the solvents under reduced pressure, the concentrate was lyophilized. There was thus obtained 4.0 g. of 1-(5'-O-palmitoyl-β-D-arabinofuranosyl)-N⁴-[N-[N-[N-(tert-butoxycarbonyl)glycyl]glycyl]-L-phenylalanyl]cytosine having optical rotation $[\alpha]_D^{25} = +46°$ (c 1.1 in methanol)

Analysis: Calc'd. for $C_{43}H_{66}N_2O_{11}$: C, 61.26; H, 7.89; N, 9.97. Found: C, 61.41; H, 8.34; N, 10.57.

The NMR and IR spectra were reasonable for the proposed structure.

EXAMPLE 3

Preparation of
1-(5'-O-benzoyl-β-D-arabinofuranosyl)-N⁴-[Nα -[N-(tert-butoxycarbonyl)glycyl]-L-arginyl]cytosine hydrochloride Following the procedure of Example 1, but substituting 1-(5'-O-benzoyl-β-D-arabinofuranosyl)cytosine hydrochloride for 1-(5'-O-palmitoyl-β-D-arabinofuranosyl)cytosine hydrochloride there was prepared 1-(5'-O-benzoyl-β-D-arabinofuranosyl)-N⁴-[Nα -[N-(tert-butoxycarbonyl)glycyl]-L-arginyl]-cytosine hydrochloride.

EXAMPLE 4

Preparation of
1-(5'-O-adamantoyl-β-D-arabinofuranosyl)-N⁴-[Nα -[N-(tert-butoxycarbonyl)-glycyl]-L-arginyl]cytosine hydrochloride Following the procedure of Example 1, but substituting 1-(5'-O-adamantoyl-β-D-arabinofuranosyl)cytosine hydrochloride for 1-(5'-O-palmitoyl-β-D-arabinofuranosyl)cytosine hydrochloride, there was prepared 1-(5'-O-adamantoyl-β-D-arabinofuranosyl)-N⁴-[Nα -[N-(tert-butoxycarbonyl)glycyl]-L-arginyl]-cytosine hydrochloride.

EXAMPLE 5

Following the procedure of Example 1, but substituting separately, 1-(5'-O-anisoyl-β-D-arabinofuranosyl)cytosine hydrochloride, 1-(5'-O-acetyl-β-D-arabinofuranosyl)cytosine hydrochloride, 1-(5'-O-propionyl-β-D-arabinofuranosyl)cytosine hydrochloride, 1-(5'-O-sec-butyryl-β-D-arabinofuranosyl)cytosine hydrochloride, 1-(5'-O-tetradecyl-β-D-arabinofuranosyl)cytosine hydrochloride, 1-(5'-O-eicosyl-β-D-arabinofuranosyl)cytosine hydrochloride, 1-(5'-O-α,α, α-trifluoroacetyl-β-D-arabinofuranosyl)-cytosine hydrochloride, 1-(5'-o-α-ethoxyacetyl-β-D-arabinofuranosyl)cytosine hydrochloride, 1-(5'-O-α-phenylacetyl-β-D-arabinofuranosyl)cytosine hydrochloride, 1-(5'-O-α-cyclohexylcarbonyl-β-D-arabinofuranosyl)-cytosine hydrochloride, 1-(5'-O-p-toluoyl-β-D-arabinofuranosyl)cytosine hydrochloride, and 1-(5'-O-o-chlorobenzoyl-β-D-arabinofuranosyl)cytosine hydrochloride for 1-(5'-O-palmitoyl-β-D-arabinofuranosyl)cytosine, there is prepared the corresponding 1-(5'-O-anisoyl-β-D-arabinofuranosyl)-N⁴-[Nα -[N-(tert-butoxycarbonyl)glycyl]-L-arginyl]cytosine hydrochloride, 1-(5'-O-acetyl-β-D-arabinofuranosyl)-N⁴-[Nα -[N-(tert-butoxycarbonyl)glycyl]-L-arginyl]cytosine hydrochloride, 1-(5'-O-propionyl-β-D-arabinofuranosyl)-N⁴-[Nα -[N-(tert-butoxycarbonyl)glycyl]-L-arginyl]cytosine hydrochloride, 1-(5'-O-sec-butyryl-β-D-arabinofuranosyl)-N⁴-[Nᵅ -[N-(tert-butoxycarbonyl)glycyl]-L-arginyl]cytosine hydrochloride, 1-(5'-O-tetradecyl-β-D-arabinofuranosyl)-N⁴-[Nᵅ -[N-(tert-butoxycarbonyl)glycyl]-L-arginyl]cytosine hydrochloride, 1-(5'-O-eicosyl-β-D-arabinofuranosyl)-N⁴-[Nᵅ -[N-(tert-butoxycarbonyl)glycyl]-L-arginyl]cytosine hydrochloride, 1-(5'-O-α,α,α-trifluoroacetyl-β-D-arabinofuranosyl)-N⁴-[Nᵅ -[N-(tert-butoxycarbonyl)glycyl]-L-arginyl]cytosine hydrochloride, 1-(5'-O-α-ethoxyacetyl-β-D-arabinofuranosyl)-N⁴-[Nᵅ -[N-(tert-butoxycarbonyl)glycyl]-L-arginyl]cytosine hydrochloride, 1-(5'-O-α-phenylacetyl-β-D-arabinofuranosyl)-N⁴-[Nᵅ -[N-(tert-butoxycarbonyl)glycyl]-L-arginyl]cytosine hydrochloride, 1-(5'-O-α-cyclohexylcarbonyl-β-D-arabinofuranosyl)-N⁴-[Nᵅ -[N-(tert-butoxycarbonyl)glycyl]-L-arginyl]cytosine hydrochloride, 1-(5'-O-p-toluoyl-β-D-arabinofuranosyl)-N⁴-[Nᵅ -[N-(tert-butoxycarbonyl)glycyl]-L-arginyl]cytosine hydrochloride, and 1-(5'-O-o-chlorobenzoyl-β-D-arabinofuranosyl)-N⁴-[Nᵅ -[N-(tert-butoxycarbonyl)glycyl]-L-arginyl]cytosine hydrochloride, respectively.

EXAMPLE 6

Following the procedure of Example 1, but substituting, separately,

N-(tert-butoxycarbonyl)valine,
N-(tert-butoxycarbonyl)phenylalanine,
Nᵅ -(tert-butoxycarbonyl)-L-arginine,
N-(tert-butoxycarbonyl)glycine,
N,N-di-(tert-butoxycarbonyl)lysine,
N-(tert-butoxycarbonyl)serine, and
Nᵅ -[N-[N-[N-[N-[N-(tert-butoxycarbonyl)glycyl]-glycyl]glycyl]glycyl]glycyl]glycyl]-L-arginine, for Nᵅ -[N-(tert-butoxycarbonyl)glycyl]-L-arginine, there is prepared the corresponding 1-(5'-O-palmitoyl-β-D-arabinofuranosyl)-N⁴-[N-(tert-butoxycarbonyl)valyl]cytosine, 1-(5'-O-palmitoyl-β-D-arabinofuranosyl)-N⁴-[N-(tert-butoxycarbonyl)phenylalanyl]cytosine, 1-(5'-O-palmitoyl-β-D-arabinofuranosyl)-N⁴-[Nᵅ -(tert-butoxycarbonyl)-L-arginyl]cytosine hydrochloride, 1-(5'-O-palmitoyl-β-D-arabinofuranosyl)-N⁴-[N-(tert-butoxycarbonyl)glycyl]cytosine.

1-(5'-O-palmitoyl-β-D-arabinofuranosyl)-N⁴-[N,N-di-(tert-butoxycarbonyl)lysyl]cytosine, 1-(5'-o-palmitoyl-β-D-arabinofuranosyl)-N⁴-[N-(tert-butoxycarbonyl)seryl]cytosine, and 1-(5'-O-palmitoyl-β-D-arabinofuranosyl)-N⁴-[Nᵅ -[N-[N-[N-[N-[N-(tert-butoxycarbonyl)glycyl]-glycyl]glycyl]glycyl]-glycyl]glycyl]-L-arginyl]cytosine hydrochloride, respectively.

EXAMPLE 7

Following the procedure of Example 1, but substituting, separately, 1-(5'-O-palmitoyl-β-D-arabinofuranosyl)-5-iodocytosine hydrochloride, 1-(5'-O-palmitoyl-β-D-arabinofuranosyl)-5-methylcytosine hydrochloride, and 1-(5'-O-palmitoyl-β-D-arabinofuranosyl)-5-trifluoromethylcytosine hydrochloride, for 1-(5'-O-palmitoyl-β-D-arabinofuranosyl)cytosine hydrochloride there is prepared the corresponding, 1-(5'-O-palmitoyl-β-D-arabinofuranosyl)-N⁴-[Nᵅ -[N-(tert-butoxycarbonyl)glycyl]-L-arginyl]-5-iodocytosine hydrochloride, 1-(5'-O-palmitoyl-β-D-arabinofuranosyl)-N⁴-[Nᵅ -[N-(tert-butoxycarbonyl)glycyl]-L-arginyl]-5-methylcytosine hydrochloride, and 1-(5'-O-palmitoyl-β-D-arabinofuranosyl)-N⁴-[Nᵅ -[N-(tert-butoxycarbonyl)glycyl]-L-arginyl]-5-trifluoromethylcytosine hydrochloride, respectively.

The new 1-(3'-O-, 5'-O-, and 3',5'-O,O-Variable-β-D-arabinofuranosyl)-N⁴-(α-aminoacyl)cytosines of this invention (Compounds according to Formula I) are active antiviral, antitumor, and immunosuppressant agents. They can be administered to animals in many different formulations. Some such formulations will produce better results than others depending upon many physiological variables. Nevertheless, guidelines can be provided. In general, oral administration is a convenient route, but intramuscular, intraperitoneal, subcutaneous, topical, and intravenous routes are contemplated.

For oral administration, a compound or a mixture of compounds of this invention can be encapsulated or tableted so as to provide a unit dosage, containing about 3 to about 1000 mg. of active ingredient per unit. The various unit dosages can be administered singly, severally, and sequentially so as to provide continuing chemotherapy. A fluid form can also be administered orally as a unit dosage by measured volume.

The amount of any dosage will depend upon many factors among them being the kind, age, weight, sex, and physical condition of the animal. The nature of the affliction and its severity are paramount considerations. In general, a total dosage of from about 0.1 mg. to about 50.0 mg. per kilogram of body weight is contemplated. A total daily dosage may range from about 3 mg. to about 4000 mg.

If intramuscular or intraperitoneal injections are to be used, a compound of the invention, or a mixture of compounds, can be dissolved or dispersed in liquid media, for example, water, oils such as peanut oil, cottonseed oil, and sesame seed oil, and physiological saline solutions. Other components can be included in the foregoing suggested solutions and dispersions. Solubilizing agents, surfactants, and other physiological adjuvants can be included.

These injectable dosage forms are administered singly or in multiples so that any desired chemotherapeutic regimen is achieved. In general, injections of from about 1 ml. to about 10 ml. are contemplated.

Further with respect to oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Tablets can be enterically coated or uncoated. Wafers are prepared in the same manner as tablets, differing only in shape and the inclusion of sucrose or other sweetener and flavor. In their simplest embodiment, capsules, like tablets, are prepared by mixing the active compound of the formulation with an inert pharmaceutical diluent and filling the mixture into a hard gelatin capsule of appropriate size. In another embodiment, capsules are prepared by filling hard gelatin capsules with polymer coated beads containing the active compound. Soft gelatin capsules are prepared by machine encapsulation of a slurry of the active compound with an acceptable vegetable oil, light liquid petrolatum or other inert oil.

Fluid unit dosage forms for oral administration such as syrups, elixirs, and suspensions can also be prepared. The water-soluble forms of the active compound can be dissolved in an aqueous vehicle together with an aromatic flavoring agent, if desired. Suspensions can be prepared of the insoluble forms with a syrup vehicle with the aid of a suspending agent such as acacia, tragacanth, methylcellulose and the like.

EXAMPLE 8

Tablets for oral administration 1000 scored tablets for oral use, each containing 500 mgs. of 1-(5'-O-palmitoyl-$\beta$-D-arabinofuranosyl)-$N^4$-[$N^\alpha$ -[N-(tert-butoxycarbonyl)glycyl]-L-arginyl]-cytosine hydrochloride are prepared from the following types and amounts of ingredients:

| | |
|---|---|
| 1-(5'-O-palmitoyl-$\beta$-D-arabinofuranosyl)-$N^4$-[$N^\alpha$ -[N-tert-butoxycarbonyl)glycyl]-L-arginyl]cytosine HCl | 500 Gms. |
| Starch, U.S.P. | 35 Gms. |
| Talc, U.S.P. | 25 Gms. |
| Calcium stearate | 3.5 Gms. |

The powdered active ingredient is granulated with a 4% w/v aqueous solution of methylcellulose 1500 cps. U.S.P. To the dried granules is added a mixture of the remainder of the ingredients and the final mixture is compressed into tablets of approximately 560 mg. weight.

EXAMPLE 9

Infusable preparation

A sterile aqueous preparation suitable for intravenous infusion and containing 25 mg. of 1-(5'-O-palmitoyl-$\beta$-D-arabinofuranosyl)-$N^4$-[$N^\alpha$ -[N-(tert-butoxycarbonyl)glycyl]L-arginyl]cytosine HCl in each 2 mls. is prepared from the following ingredients:

| | |
|---|---|
| 1-(5'-O-palmitoyl-$\beta$-D-arabinofuranosyl)-$N^4$-[$N^\alpha$ -[N-(tert-butoxycarbonyl)glycyl]-L-arginyl]cytosine HCl | 12.5 Gms. |
| Polyethylene glycol 4000 U.S.P. | 30 Gms. |
| Sodium chloride U.S.P. | 9 Gms. |
| Preservative | q.s. |
| Water for injection q.s. | 1000 ml. |

This invention embraces both the realistic embodiments described herein and the reasonable extensions thereof as contemplated herein. Therefore, in accordance with the Law of Patents as set forth in the various published decisions extant, this invention is not to be interpreted solely in terms of the embodiments and obvious extensions thereof that are specifically described. Equivalent modifications thereof are includable. The claims provide primary guidelines for the limits of the invention and basis for equivalent extensions thereof.

We claim:

1. The compounds 1-(3'-O-Variable- and 5'-O-Variable-$\beta$-D-arabinofuranosyl)-$N^4$-($\alpha$-aminoacyl)cytosines of the formula:

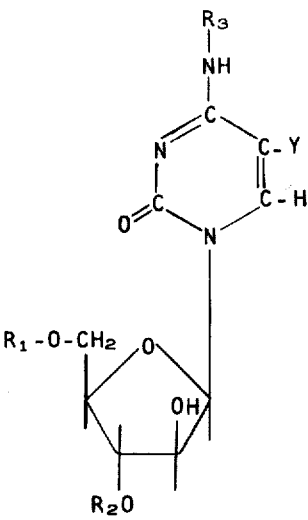

wherein $R_1$ and $R_2$ are hydrogen, or an acyl group comprising up to 21 carbon atoms, inclusive; Y is hydrogen, halogen, or alkyl-, hydroxyalkyl-, or haloalkyl of from 1 to 4 carbon atoms, inclusive; and $R_3$ is an $\alpha$-aminoacyl group consisting of a single $\alpha$-amino acid or up to 10 $\alpha$-aminoacids linked as peptides, including acid addition salts thereof.

2. The compounds according to claim 1 wherein $R_2$ is hydrogen.

3. The compounds according to claim 2 wherein Y is hydrogen.

4. The compounds according to claim 3 wherein $R_1$ is carboxylic acyl.

5. The compounds according to claim 4 wherein the $\alpha$-aminoacyl group comprises -L-arginine, phenylalanine, or lysine attached to the 4-nitrogen of the cytosine.

6. The compounds according to claim 5 wherein the $\alpha$-aminoacyl group comprises glycine and arginine or glycine and phenylalanine.

7. The compounds according to claim 6 wherein the $\alpha$-aminoacyl group is $N^\alpha$ -[N-(tert-butoxycarbonyl)-glycyl]-L-arginyl.

8. The compounds according to claim 7 wherein the 5'-O-carboxylic acyl group is palmitoyl, benzoyl, adamantoyl, or cyclohexane carbonyl.

9. The compound according to claim 8, 1-(5'-O-palmitoyl-$\beta$-D-arabinofuranosyl)-$N^4$-[$N^\alpha$ -[N-(tert-butoxycarbonyl)glycyl]-L-arginyl]cytosine hydrochloride.

10. The compound according to claim 8, 1-(5'-O-palmitoyl-$\beta$-D-arabenofuranosyl)-$N^4$-[N-[N-(tert-butoxycarbonyl)-glycyl]glycyl]-L-phenylalanyl]cytosine.

11. The compound according to claim 8, 1-(5'-O-benzoyl-$\beta$-D-arabinofuranosyl)-$N^4$-[$N^\alpha$ -[N-(tert-butoxycarbonyl)glycyl]L-arginyl]cytosine hydrochloride.

12. The compound according to claim 8, 1-(5'-O-adamantoyl-$\beta$-D-arabinofuranosyl)-$N^4$-[$N^\alpha$ -[N-(tert-butoxycarbonyl)glycyl]L-arginyl]cytosine hydrochloride.

* * * * *